US011445933B2

(12) United States Patent
Moeller et al.

(10) Patent No.: US 11,445,933 B2
(45) Date of Patent: Sep. 20, 2022

(54) EFFICIENT MULTI-SHOT EPI WITH SELF-NAVIGATED SEGMENTATION

(71) Applicant: REGENTS OF THE UNIVERSITY OF MINNESOTA, Minneapolis, MN (US)

(72) Inventors: Steen Moeller, Minneapolis, MN (US); Sudhir Ramanna, Minneapolis, MN (US); Mehmet Akcakaya, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 325 days.

(21) Appl. No.: 16/858,926

(22) Filed: Apr. 27, 2020

(65) Prior Publication Data

US 2020/0337588 A1 Oct. 29, 2020

Related U.S. Application Data

(60) Provisional application No. 62/838,533, filed on Apr. 25, 2019.

(51) Int. Cl.

| | |
|---|---|
| ***A61B 5/055*** | (2006.01) |
| ***G01R 33/46*** | (2006.01) |
| ***G01R 33/56*** | (2006.01) |
| ***G01R 33/561*** | (2006.01) |
| ***G01R 33/36*** | (2006.01) |
| ***G01R 33/48*** | (2006.01) |

(52) U.S. Cl.

CPC .......... *A61B 5/055* (2013.01); *G01R 33/3607* (2013.01); *G01R 33/4625* (2013.01); *G01R 33/4826* (2013.01); *G01R 33/5608* (2013.01); *G01R 33/5611* (2013.01); *G01R 33/5616* (2013.01); *G01R 33/5618* (2013.01)

(58) Field of Classification Search

CPC ........... G01R 33/3607; G01R 33/4625; G01R 33/4826; G01R 33/5608; G01R 33/5611; G01R 33/5616; G01R 33/5618; A61B 5/055

See application file for complete search history.

(56) References Cited

U.S. PATENT DOCUMENTS

| | | | | |
|---|---|---|---|---|
| 10,634,752 | B2 * | 4/2020 | Li | G01R 33/5635 |
| 2013/0181712 | A1 * | 7/2013 | Sutton | G01R 33/5676 324/314 |
| 2019/0369199 | A1 * | 12/2019 | Setsompop | G01R 33/5616 |

* cited by examiner

*Primary Examiner* — Gregory H Curran
(74) *Attorney, Agent, or Firm* — Quarles & Brady LLP

(57) ABSTRACT

Magnetic resonance imaging ("MRI") data are corrected from corruptions due to physiological changes using a self-navigated phase correction technique. Unlike motion correction techniques, the effects of physiological changes (e.g., breathing and respiration) are corrected by making the MRI data self-consistent relative to an absolute uncorrupted phase reference. This phase correction information can be extracted from the acquisition itself, thereby eliminating the need for a separate navigator scan, and establishing an accelerated acquisition. This absolute reference can be computed in a data segmented space, and the subsequent data can be corrected relative to this absolute reference with low-resolution phases.

26 Claims, 5 Drawing Sheets

302 ACCESS SEGMENTED 3D k-SPACE DATA

304 ESTIMATE REFERENCE PHASE FOR EACH $k_z$-PLANE

306 CALCULATE $k_z$-DEPENDENT PHASE VALUES

308 COMPUTE PHASE DIFFERENCE VALUES

310 APPLY PHASE DIFFERENCES TO EACH CHANNEL TO CORRECT k-SPACE DATA

312 RECONSTRUCT IMAGE(S)

EFFICIENT MULTI-SHOT EPI WITH SELF-NAVIGATED SEGMENTATION

CROSS-REFERENCE TO RELATED APPLICATIONS

This application claims the benefit of U.S. Provisional Patent Application Ser. No. 62/838,533, filed on Apr. 25, 2019, and entitled "EFFICIENT MULTI-SHOT EPI WITH SELF-NAVIGATED SEGMENTATION," which is herein incorporated by reference in its entirety.

STATEMENT REGARDING FEDERALLY SPONSORED RESEARCH

This invention was made with government support under EB025144, EB015894, NS076408, HL111410, and OD017974, awarded by National Institutes of Health. The government has certain rights in the invention.

BACKGROUND

The use of multi-shot encoding in MRI is used in readout-segmented EPI, phase-encoding segmented EPI, and 3D segmented EPI. The sensitivity of EPI to field variations reduces the effectiveness of segmented EPI acquisitions, and for either a 2D or 3D segmented EPI acquisitions, the need for correcting for physiologically induced phase variations between segments requires computational approaches and/or additional measurements, such as 2D navigators. Such additional measurements reduce the efficiency of segmented approaches by 30-50% and are SNR dependent.

SUMMARY OF THE DISCLOSURE

The present disclosure addresses the aforementioned drawbacks by providing a method for reconstructing an image of a subject from k-space data acquired with a magnetic resonance imaging (MRI) system. The method includes accessing k-space data acquired from a subject using an MRI system. The k-space data are segmented k-space data including a plurality of k-space segments (e.g., a plurality of $k_z$-planes, a plurality of k-space blades). Reference phase maps are estimated for each k-space segment. Also, k-space segment-dependent phase values are calculated from the k-space data. Phase difference values are calculated for each k-space segment using the reference phase map for that k-space segment and the corresponding k-space segment-dependent phase values. Phase corrected k-space data are generated by applying the phase difference values to the k-space data in order to reduce phase corruptions caused by physiological changes in the subject that when the k-space data were acquired. An image is then reconstructed from the phase corrected k-space data.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Figure 1:
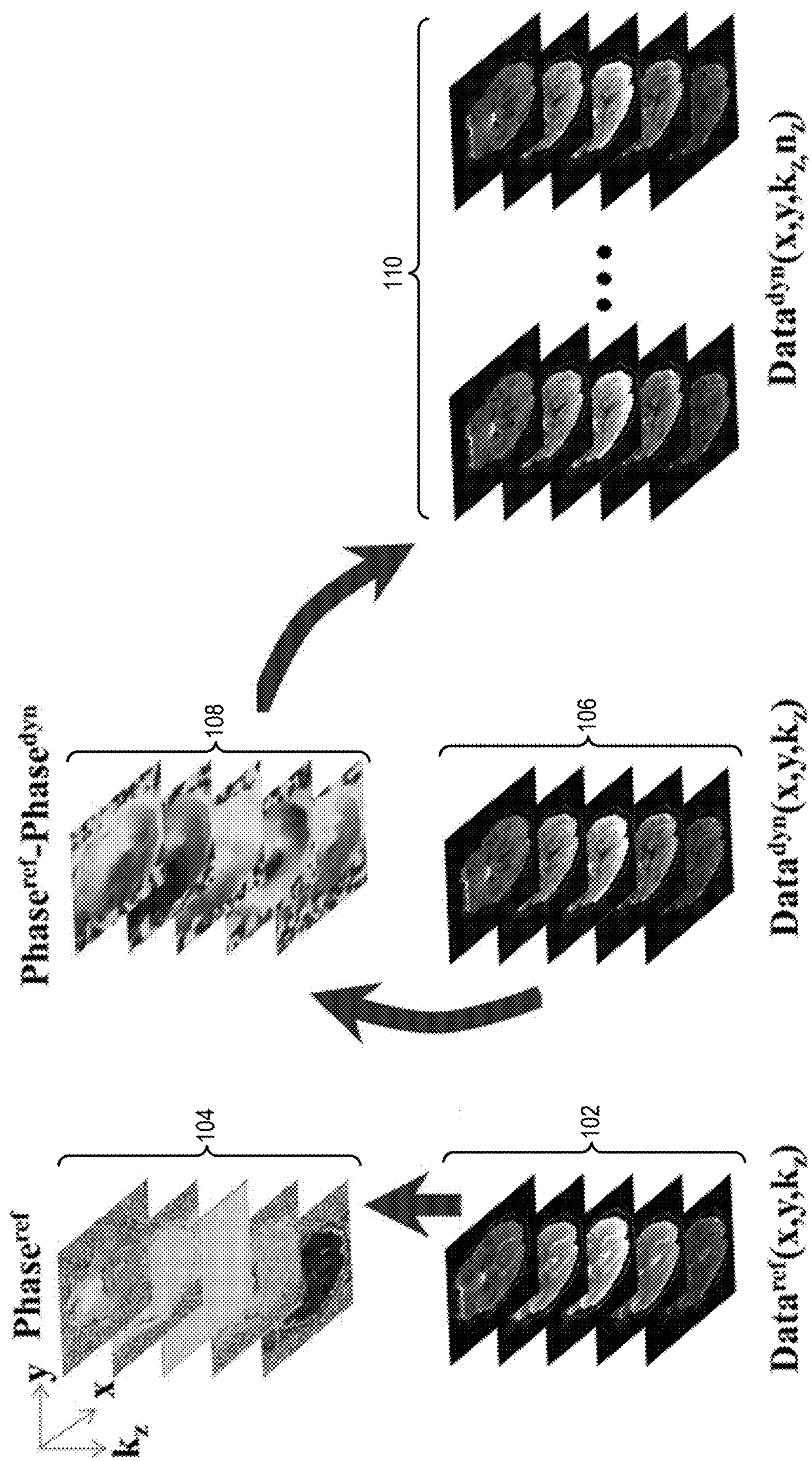
FIG. 1 is a flow diagram for an example implementation of the self-navigated phase correction methods described in the present disclosure.

Described here are systems and methods for correcting magnetic resonance imaging ("MRI") data from corruptions due to physiological changes. Unlike motion correction techniques, the systems and methods described in the present disclosure correct the effects of physiological changes (e.g., breathing and respiration) by making the MRI data self-consistent relative to an absolute uncorrupted phase reference. This phase correction information can be extracted from the acquisition itself, thereby eliminating the need for a separate navigator scan, and establishing an accelerated acquisition. As will be described, this absolute reference can be computed in a data segmented space, and the subsequent data can be corrected relative to this absolute reference with low-resolution phases.

The systems and methods described in the present disclosure are particularly advantageous for resolving corrupted data due to the effects of breathing or other physiological changes during the application of diffusion encoding gradients in a diffusion weighted imaging ("DWI") sequence. In this way, methods are provided for self-navigation of DWI techniques, which may include 3D DWI techniques such as diffusion weighted 3D multislab multiband SE-EPI, to enable whole brain high-resolution imaging.

In some example implementations described in the present disclosure, a self-navigated approach for correcting modulations in $k_z$-segmented 3D EPI is provided. This technique enables an efficient real-time processing for integration into existing 3D reconstruction frameworks, and is suitable for high b-value/low SNR protocols. Use of self-navigation for removing macroscopic sensitivity to $B_0$-induced phase variations from physiology eliminates the need for 2D navigators, increasing efficiency. Additionally, a combination with SMS/MB can be used to simultaneously excite multiple slabs (e.g., multislab-multiband) for large FOV coverage at optimal TRs. A SQUASHER-type encoding can also be used to introduce quadratic phase across the slab, thereby spreading the signal in $k_z$ to estimate accurately the signals for self-navigation through $k_z$. Additionally, with SQUASHER, the peak power can be reduced enabling high bandwidth multiband which imparts significant advantages with respect to Fourier/sinc encoding. Use of self-navigation can also be useful for low b-value applications, like intravoxel incoherent motion ("IVIM") or pseudo diffusion, and also when measuring the diffusion in metabolites using diffusion weighted spectroscopy. Self-navigation for Hadamard-type encoding also provides a correction for each grouping of simultaneously acquired slices.

As a non-limiting example, the systems and methods described in the present disclosure can be implemented with segmented 3D acquisitions, such as a segmented 3D echo planar imaging ("EPI") acquisition. In such acquisitions, slab-selective RF pulses are used to select a slab in one direction (e.g., the z-direction) and the resulting precessing magnetization is detected with a 2D acquisition in the x- and y-directions. For instance, the 2D acquisition can be a single EPI echo train encoding in two dimensions using readout and phase encoding gradients, or in another instance of a 2D non-Cartesian encoding. The 2D acquisition can be triggered by a separate measurement of physiological motion to minimize the motion difference between echo trains.

In some instances, the 2D acquisition (e.g., the 2D encoded echo train) can be undersampled along the phase encoding dimension (e.g., in the x-direction, the y-direction, or both) for reconstruction with parallel imaging. This phase encoding can be referred to as the "in-plane" phase encoding. This excitation and subsequent detection is repeated with a second phase encoding, this time along the z-direction encoding in $k_z$, and the number of repetitions of this second phase encoding is equal to the number of slices (including any oversampling) employed to resolve the slab in the z-direction. This phase encoding along the z-direction can sometimes be referred to as partition encoding. Fourier transform along the phase encoding in the z-direction divides the slab into multiple slices (including any oversampling).

The repetition time ("TR") refers to the time between the RF pulses applied to the same volume of the sample. As an example, in multi-slab volume coverage using 3D ms-EPI, the minimum TR can be determined by the number of slabs and the acquisition time of the (x, y) encoded data from the slab. The time required for the coverage of the targeted volume (volume acquisition time, or "VAT") is given by the number of slices (including oversampling slices) employed per slab multiplied by the TR.

The systems and methods described in the present disclosure are conceptually different than the conventional navigator-based techniques, and in particular can be implemented without acquiring temporal navigators at $k_z$=0.

Conceptually, the signal with a diffusion-phase can be expressed as, $$s(\vec{k}, t) = \int \rho(\vec{x}) e^{i\vec{k}\cdot\vec{x}} e^{i\phi_t(\vec{x})} d\vec{x} = F(\rho) \otimes F\left(e^{i\phi_t(\vec{x})}\right), \quad t = 1 \ldots k_z; \tag{1}$$

where $s(\vec{k}, t)$ is the measured k-space data, $\rho(\vec{x})$ is the magnitude of the spin-distribution in the object, and $\phi_t(\vec{x})$ the phase of the spin-distribution obtained for a discrete set of experimental conditions corresponding to each echo. The phase, $\phi_t(\vec{x})$, includes both the dynamically varying diffusion-phase and the object phase. The discrete representation of the k-space data can be given as $s(\vec{k},t)=F(\rho)\Phi_t$, where $\Phi_t$ is a matrix representation of a convolutional operator. The k-space data $s(\vec{k},t)$ are corrected such that the spatially induced diffusion-phase is formally replaced with a reference phase, as follows $$s^{corrected}(\vec{k}, t) = F(\rho)\Phi_t\Phi_t^{-1}\Phi_{reference} = F(\rho) \otimes F\left(e^{i\phi_{reference}(\vec{x})}\right); \tag{2}$$

which in general is non-trivial to compute since $\Phi_t$, $\Phi_t^{-1}$, and, $\Phi_{reference}$ are each large convolutional operators. Instead of obtaining explicit representations for $\Phi_t^{-1}$ and $\Phi_{reference}$, the integrated effect of $(\Phi_t^{-1}\Phi_{reference})[k_z]$ for each hybrid plane can be used for correcting Eqn. (1). The effect of the diffusion phase $\Phi_t^{-1}\Phi_{reference}$ can be assumed to be smooth in each plane of the hybrid space, $(x,y,k_z)$.

For diffusion weighted segmented 3D acquisitions, the data acquired without diffusion weighting (i.e., the b=0 s/mm$^2$ acquisition) have the least amount of diffusion-phase. Thus, in DWI applications, this non-diffusion-weighted data can be used as the phase reference, $\Phi_{reference}$.

As a first step, a channel-independent reference phase is estimated for each $k_z$-plane as, $$Data^{ref}(x, y, k_z) = \sum_{n=1}^{N} \overline{C_n(x, y)} F_{k_x,k_y}(s_n^{b=0}(k_x, k_y, k_z)); \tag{3}$$

where $s_n^{b=0}$ is the acquired echo for b=0 s/mm$^2$; $F_{k_x,k_y}$ are Fourier transformations along readout and phase-encoding directions, respectively; $C_n$ is the sensitivity profile for the slab obtained using an echo from $k_z$=0; and N is the number of channels.

The same estimation can be used for other diffusion weightings as, $$Data^{b_i}(x, y, k_z) = \sum_{n=1}^{N} \overline{C_n(x, y)} F_{k_x,k_y}\left(s_n^{b_i}(k_x, k_y, k_z)\right); \tag{4}$$

for $b_i$>0 s/mm$^2$, where each echo train for each $k_z$-plane in $s_n^{b_i}$ is acquired with different experimental conditions (e.g., diffusion-phase).

The correction $\Phi_t^{-1}\Phi_{reference}[k_z]$ is the phase-difference, $$\phi(x,y,k_z) = \angle(Data^{ref}(x,y,k_z), Data^{b_i}(x,y,k_z)) \tag{5;}$$

where $Data^{ref}(x,y,k_z)$ is obtained from Eqn. (3) using a reference acquisition and $Data^{b_i}(x,y,k_z)$ is obtained from Eqn. (4) using the diffusion-weighted acquisition.

After obtaining the channel-independent correction phase $\phi(x,y,k_z)$, each channel is corrected with $\phi(x,y,k_z)$ to impose a consistent object phase across all channels, while maintaining the channel specific phase-variations, such that the corrected channels $\tilde{s}_n^{b_i}$ are, $$\tilde{s}_n^{b_i} = F_{x,y}([F_{k_x,k_y} s_n^{b_i}(k_x,k_y,k_z)] e^{\phi(x,y,k_z)}) \tag{6.}$$

To reduce the influence of noise, the channel independent diffusion-phase $\phi(x,y,k_z)$ can be filtered prior to application. As one example, the phase can be filtered with a Gaussian filter with FWHM=4 and width 10 for each $k_z$-plane.

Following the self-navigation correction and inverse Fourier transform along $k_z$, a weighted average can be used, as one non-limiting example, to combine the data along slab boundaries, where the weights are determined using a slab profile estimate.

FIG. 1 shows a flow diagram of an example self-navigation correction according to some implementations described in the present disclosure. For each $k_z$-plane of a reference acquisition, a channel combined image 102 is calculated. For example, the channel combined images 102 can be calculated using Eqn. (3). From the channel combined image 102, a reference phase 104 for each $k_z$-plane is calculated. For the diffusion weighted image 106, a similar channel combined image is calculated, and the filtered phase-difference 108 is obtained. For example, the filtered phase-difference can be obtained using Eqn. (5). The resultant phase-difference 108 is applied identically and independently to each channel to generate the corrected images 110.

Figure 2:
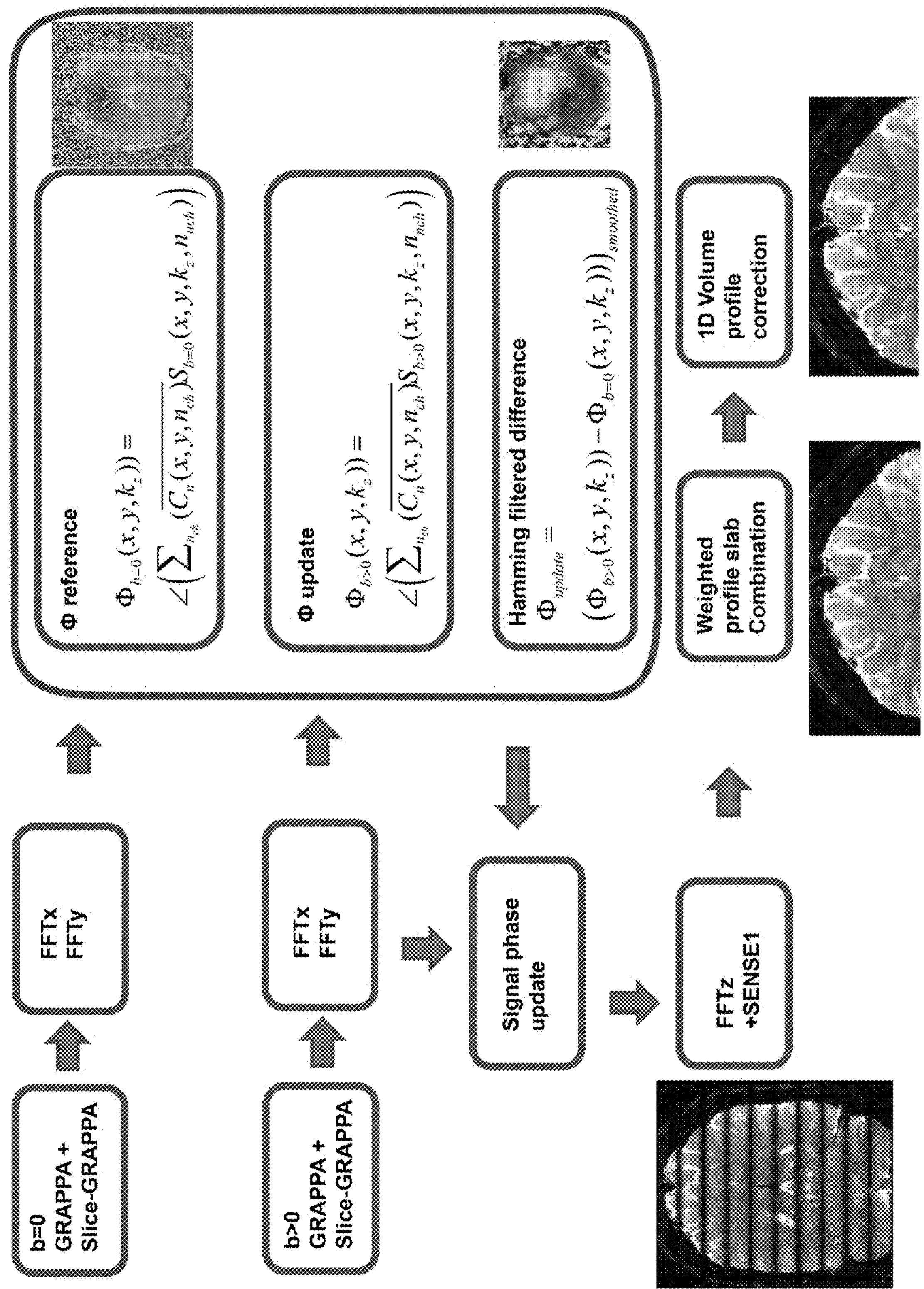
FIG. 2 is a flow diagram of another example implementation of the self-navigated phase correction methods described in the present disclosure.

FIG. 2 shows another example flow diagram of a reconstruction pipeline. The self-navigation is the phase update in steps 3 and 4, with a Hamming window filtered phase. In FIG. 2, $C_n$ are the slab wise sensitivity profiles. The 1D whole volume correction uses a smooth profile function for reference to update. Parallel imaging reconstruction in $k_y$ can be implemented, for example, with GRAPPA using FLEET for ACS, and slice-GRAPPA with slice-blocking for SMS/MB unaliasing.

Figure 3:
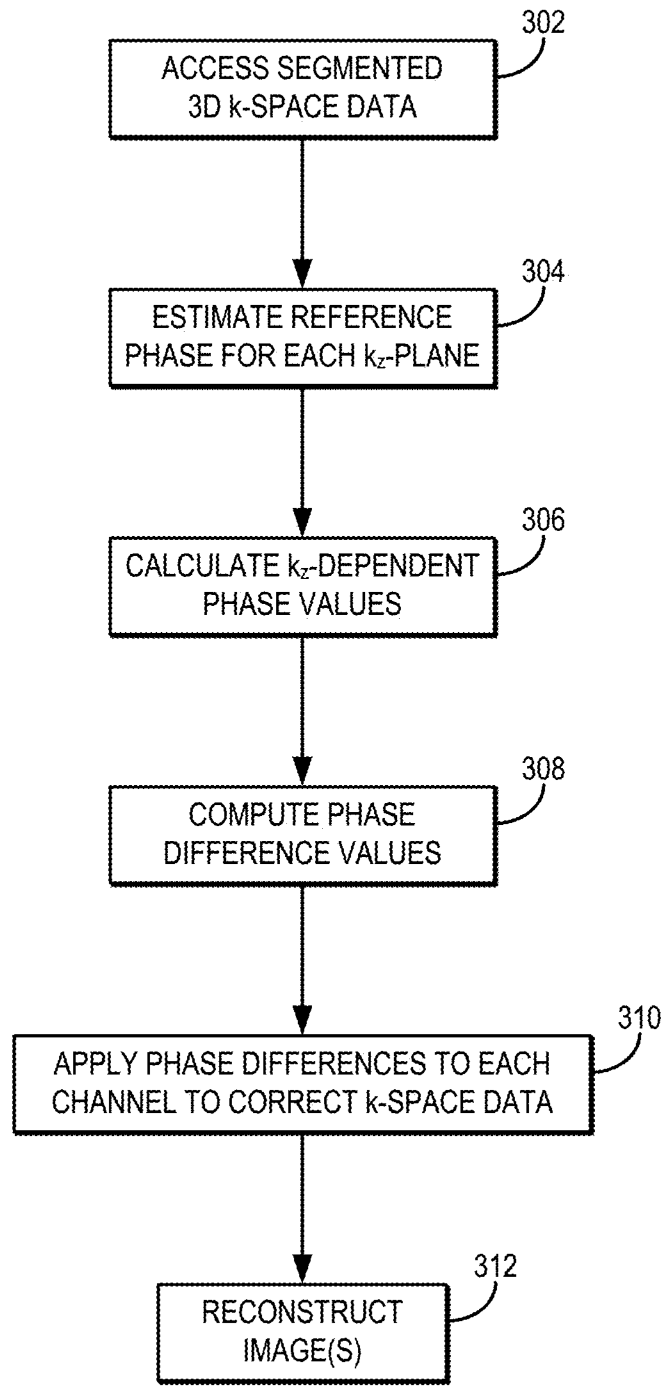
FIG. 3 is a flowchart setting for the steps of an example method for reconstructing images using the self-navigated phase correction methods described in the present disclosure.

Referring now to FIG. 3, a flowchart is illustrated as setting forth the steps of an example method for generating images from magnetic resonance data, where the images have been corrected for the effects of physiological changes as described above.

The method includes accessing magnetic resonance data with a computer system, as indicated at step 302. Accessing the magnetic resonance data can include retrieving previously acquired data from a memory or other data storage device or medium. Additionally or alternatively, accessing the magnetic resonance data can include acquiring such data with an MRI system and communicating that data to the computer system, which may be a part of the MRI system. In general, the magnetic resonance data are k-space data acquired over a plurality of k-space segments using a segmented acquisition. Using a 3D segmented acquisition, the k-space segments can be $k_z$-planes. Using a 2D or 3D readout segmented acquisition, the k-space segments can be k-space blades. In some instances, the magnetic resonance data are diffusion weighted magnetic resonance data acquired using a segmented 3D acquisition, as described above.

In some implementations, the magnetic resonance data can be acquired using a 3D segmented EPI acquisition, which may be a $k_z$-segmented, readout segmented, or phase-encoding segmented acquisition. Alternatively, the magnetic resonance data can be acquired using an echo volume imaging ("EVI") acquisition. In other instances, the magnetic resonance data can be acquired using a 2D segmented EPI acquisition, which may be a readout segmented acquisition or a phase-encoding segmented acquisition. At still another example, the magnetic resonance data can be acquired using a 2D or 3D gradient and spin echo (GRASE) acquisition.

In some embodiments, the magnetic resonance data are acquired using a pulse sequence that implements at least one multiband RF pulse. In some other embodiments, the pulse sequence can include one or more frequency swept RF pulse. In still other embodiments, the pulse sequence can implement one or more spatially selective RF pulses, one or more spectrally selective RF pulses, or both. In still other embodiments, the pulse sequence can be a 3D EPI acquisition that implements at least one 2D RF pulse. In still other embodiments, the pulse sequence can implement at least one composite RF pulse. As an example, a composite RF pulse can include a plurality of sub-pulses (e.g., sinc, HSn) with an outer envelope modulation to create 2D selectivity.

The magnetic resonance data can be acquired using Cartesian or non-Cartesian sampling patterns. For instance, non-Cartesian sampling patterns may include sampling patterns associated with 2D radials, 2D rosettes, radial FSE, a stack of 2D cylindrical GRASE, or a stack of 2D propellers.

As described, in some implementations the magnetic resonance data are diffusion-weighted magnetic resonance data. In some instances, the diffusion-weighted magnetic resonance data can be acquired using inner volume imaging with diffusion encoding.

As one non-limiting example, in an example study diffusion-weighted data were acquired on healthy volunteers using a 32-channel receiver head-coil on a 3T MRI system equipped with 80 mT/m gradients with a slew rate of 200 T/m/s. Data were acquired in this example using the following parameters.

MB1: Excitation/Refocusing=HS2R12/HS2R14, duration 7680 μs, 1 $mm^3$, TE/TR of 92.2/1610 ms with 12 slice/slab, 10 slabs, FOV 210×210×120 $mm^3$, iPAT=2, Volume acquisition time (VAT)=26 s (TR=9.5 s for an equivalent 2D SMS/MB coverage with [MB×iPAT=2×2])

MB2: Excitation/Refocusing=HS2R10/HS2R12, duration 7680 μs, 1 $mm^3$, TE/TR of 92.4/1500 ms with 10 slice/slab, 16 slabs, FOV 210×210×160 $mm^3$, iPAT=2, VAT=21 s (TR=12.5 s for an equivalent 2D SMS/MB coverage with [MB×iPAT=2×2])).

For the prescribed whole brain FOV using MB1 the 3D sequence has a 300% longer VAT compared to a 2D SMS sequence, but the 3D sequence has 16 more averages. For the larger FOV the 3D MB2 acquisition has 70% longer VAT, and 14 more averages than the 2D acquisition. The excitation profiles were designed with one slice overlap, and acquisition was with two slice oversampling A reference phase map is generated, as indicated at step 304. As an example, for each k-space segment (e.g., $k_z$-plane, k-space blade) represented in the magnetic resonance data, a relative phase reference map can be calculated from relatively uncorrupted data, such as the data acquired without diffusion weighting (i.e., the b=0 acquisition). As described above, a reference phase map can be calculated from a channel combined image using Eqn. (3).

A k-space segment-dependent (e.g., $k_z$-dependent, k-space blade-dependent) phase is then calculated for each weighting-space segment, as indicated at step 306. For diffusion weighted data, k-space segment-dependent phases can further be calculated for each diffusion weighting. For instance, a $k_z$-dependent phase can be calculated using Eqn. (4). The k-space segment-dependent phases can then be updated with a low-pass filtered difference relative to the reference phase, as indicated at step 308. As an example, the phase difference can be calculated using Eqn. (5).

The estimated phase difference is then applied to each channel to correct for the effects of physiological changes, as indicated at step 310. From these self-navigation corrected data one or more images can be reconstructed, as indicated at step 312. These images will be free from the deleterious effects of physiological changes (e.g., breathing or respiration) that occurred during data acquisition, such as during the application of diffusion encoding gradients.

Thus, a self-navigated approach for correcting modulations in $k_z$-segmented 3D magnetic resonance data acquisitions, or other segmented acquisitions, has been provided. As one example, the methods described here are applicable for efficient 3D SE-EPI multislab-multiband sequences and reconstruction, and can also be used with 3D GRE-EPI. In some implementations, the methods can combine quadratic slab phase, self-navigated segmentation correction, and data-driven slab banding artifact removal.

The phase-correction in the systems and methods described in the present disclosure can utilize "slab" sensitivity profiles for estimating a sensitivity-weighted phase. Advantageously, such data are already part of routine diffusion MRI acquisitions, and are acquired repeatedly during longer acquisitions. The integration of the proposed algorithm is therefore compatible with existing pipelines, without adding significant additional computation or reducing the speed of reconstruction. For the case of acquisitions with in-plane phase-encoding undersampling, GRAPPA can be applied to each $k_z$-plane independently and the self-navigation can be performed subsequently. For the use of fully sampled phase-encoding segmented acquisitions, the phase-consistency can be applied in image-space. If the number of segments in the phase-encoding direction is not too large, the self-navigation technique can be sufficient to train a joint GRAPPA reconstruction to reconstruct directly from the segmented acquisition with phase difference to combine segments without diffusion phase. In these instances, each segment is reconstructed independently, and for each a phase is calculated as described above. A GRAPPA kernel is trained to map from the segmented encoding with the calculated phase to a segmented acquisition with the same phase for all segments. The trained GRAPPA kernel is applied to the measured segmented data.

As another non-limiting example, the systems and methods descried in the present disclosure can be implemented with readout-segmented 2D EPI acquisitions. In such acquisitions, a single EPI echo train is encoded in two dimensions (e.g., by using sinusoidal readout encoding gradients covering only a select part of the readout bandwidth). Each segment is reconstructed independently and for each a phase is calculated as described above. The correction for each readout segmented blade is implemented similar to the method described above for correcting each $k_z$-plane. The removal of overlap between the blades in k-space is added to the image reconstruction of each blade. Image reconstruction of all readout segmented blades can be performed with complex summation in image space, or addition of the blades in k-space.

The self-navigation techniques described in the present disclosure can be applied to DW 3D ms-EPI obtained using standard sinc pulses for excitation and refocusing with both low and high bandwidth. In other examples, apodized sinc pulses can be used. In some other instance, the use of frequency swept pulses for the DW 3D ms-EPI can be used, but is not a necessary condition for the self-navigation.

Figure 4:
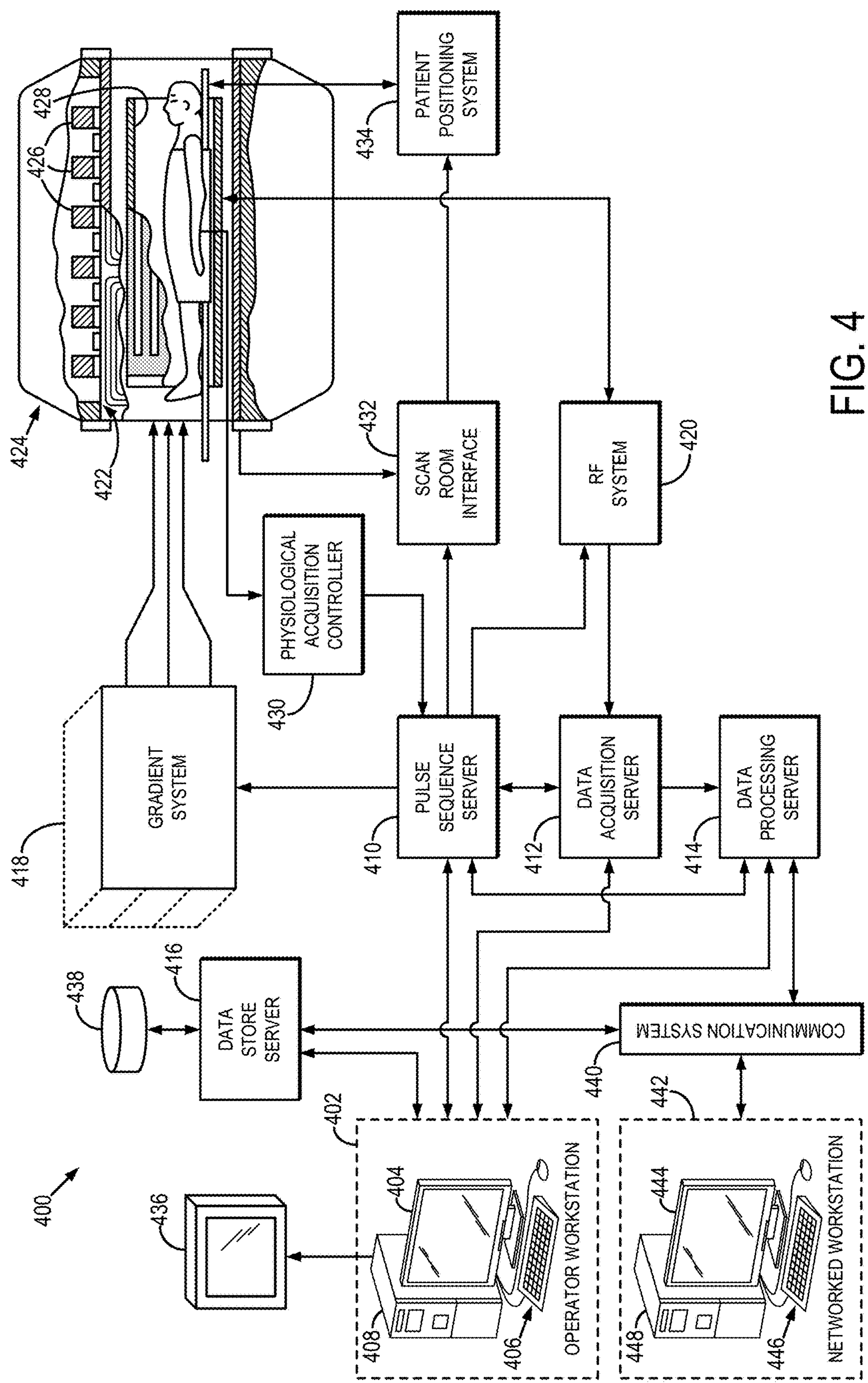
FIG. 4 is a block diagram of an example MRI system that can implement the methods described in the present disclosure.

Referring particularly now to FIG. 4, an example of an MRI system 400 that can implement the methods described here is illustrated. The MRI system 400 includes an operator workstation 402 that may include a display 404, one or more input devices 406 (e.g., a keyboard, a mouse), and a processor 408. The processor 408 may include a commercially available programmable machine running a commercially available operating system. The operator workstation 402 provides an operator interface that facilitates entering scan parameters into the MRI system 400. The operator workstation 402 may be coupled to different servers, including, for example, a pulse sequence server 410, a data acquisition server 412, a data processing server 414, and a data store server 416. The operator workstation 402 and the servers 410, 412, 414, and 416 may be connected via a communication system 440, which may include wired or wireless network connections.

The pulse sequence server 410 functions in response to instructions provided by the operator workstation 402 to operate a gradient system 418 and a radiofrequency ("RF") system 420. Gradient waveforms for performing a prescribed scan are produced and applied to the gradient system 418, which then excites gradient coils in an assembly 422 to produce the magnetic field gradients $G_x$, $G_y$, and $G_z$ that are used for spatially encoding magnetic resonance signals. The gradient coil assembly 422 forms part of a magnet assembly 424 that includes a polarizing magnet 426 and a whole-body RF coil 428.

RF waveforms are applied by the RF system 420 to the RF coil 428, or a separate local coil to perform the prescribed magnetic resonance pulse sequence. Responsive magnetic resonance signals detected by the RF coil 428, or a separate local coil, are received by the RF system 420. The responsive magnetic resonance signals may be amplified, demodulated, filtered, and digitized under direction of commands produced by the pulse sequence server 410. The RF system 420 includes an RF transmitter for producing a wide variety of RF pulses used in MRI pulse sequences. The RF transmitter is responsive to the prescribed scan and direction from the pulse sequence server 410 to produce RF pulses of the desired frequency, phase, and pulse amplitude waveform. The generated RF pulses may be applied to the whole-body RF coil 428 or to one or more local coils or coil arrays.

The RF system 420 also includes one or more RF receiver channels. An RF receiver channel includes an RF preamplifier that amplifies the magnetic resonance signal received by the coil 428 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M=\sqrt{I^2+Q^2} \quad (7);$$

and the phase of the received magnetic resonance signal may also be determined according to the following relationship:

$$\varphi=\tan^{1}\left(\frac{Q}{I}\right). \quad (8)$$

The pulse sequence server 410 may receive patient data from a physiological acquisition controller 430. Byway of example, the physiological acquisition controller 430 may receive signals from a number of different sensors connected to the patient, including electrocardiograph ("ECG") signals from electrodes, or respiratory signals from a respiratory bellows or other respiratory monitoring devices. These signals may be used by the pulse sequence server 410 to synchronize, or "gate," the performance of the scan with the subject's heart beat or respiration.

The pulse sequence server 410 may also connect to a scan room interface circuit 432 that receives signals from various sensors associated with the condition of the patient and the magnet system. Through the scan room interface circuit 432, a patient positioning system 434 can receive commands to move the patient to desired positions during the scan.

The digitized magnetic resonance signal samples produced by the RF system 420 are received by the data acquisition server 412. The data acquisition server 412 operates in response to instructions downloaded from the operator workstation 402 to receive the real-time magnetic resonance data and provide buffer storage, so that data is not lost by data overrun. In some scans, the data acquisition server 412 passes the acquired magnetic resonance data to the data processor server 414. In scans that require information derived from acquired magnetic resonance data to control the further performance of the scan, the data acquisition server 412 may be programmed to produce such information and convey it to the pulse sequence server 410. For example, during pre-scans, magnetic resonance data may be acquired and used to calibrate the pulse sequence performed by the pulse sequence server 410. As another example, navigator signals may be acquired and used to adjust the operating parameters of the RF system 420 or the gradient system 418, or to control the view order in which k-space is sampled. In still another example, the data acquisition server 412 may also process magnetic resonance signals used to detect the arrival of a contrast agent in a magnetic resonance angiography ("MRA") scan. For example, the data acquisition server 412 may acquire magnetic resonance data and processes it in real-time to produce information that is used to control the scan.

The data processing server 414 receives magnetic resonance data from the data acquisition server 412 and processes the magnetic resonance data in accordance with instructions provided by the operator workstation 402. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 414 are conveyed back to the operator workstation 402 for storage. Real-time images may be stored in a data base memory cache, from which they may be output to operator display 402 or a display 436. Batch mode images or selected real time images may be stored in a host database on disc storage 438. When such images have been reconstructed and transferred to storage, the data processing server 414 may notify the data store server 416 on the operator workstation 402. The operator workstation 402 may be used by an operator to archive the images, produce films, or send the images via a network to other facilities.

The MRI system 400 may also include one or more networked workstations 442. For example, a networked workstation 442 may include a display 444, one or more input devices 446 (e.g., a keyboard, a mouse), and a processor 448. The networked workstation 442 may be located within the same facility as the operator workstation 402, or in a different facility, such as a different healthcare institution or clinic.

The networked workstation 442 may gain remote access to the data processing server 414 or data store server 416 via the communication system 440. Accordingly, multiple networked workstations 442 may have access to the data processing server 414 and the data store server 416. In this manner, magnetic resonance data, reconstructed images, or other data may be exchanged between the data processing server 414 or the data store server 416 and the networked workstations 442, such that the data or images may be remotely processed by a networked workstation 442.

Figure 5:
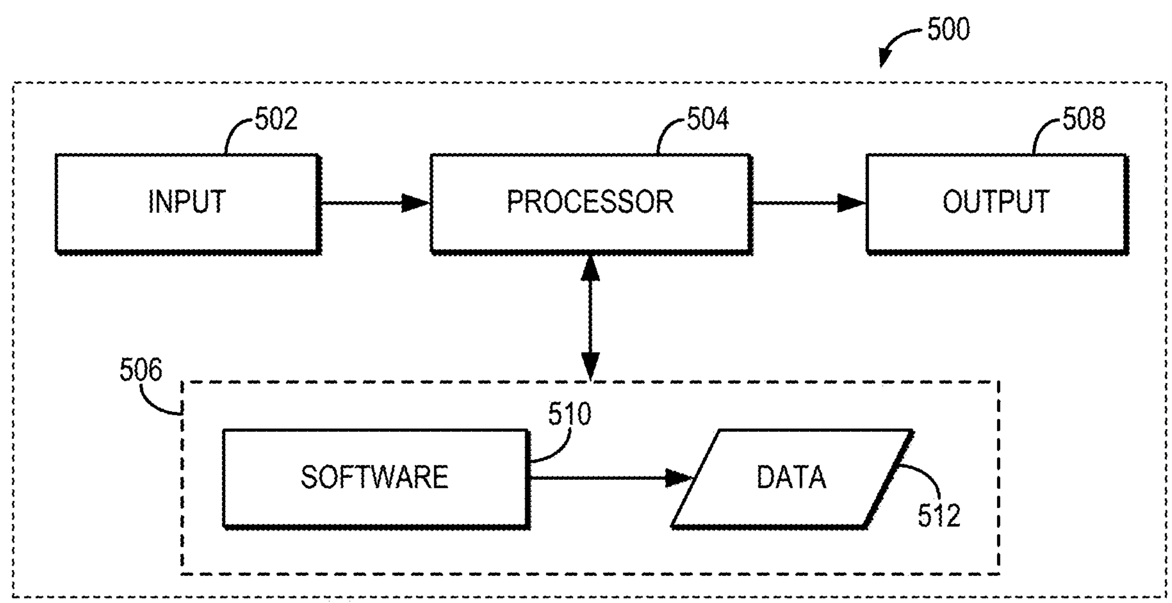
FIG. 5 is a block diagram of an example computer system that can implement the methods described in the present disclosure.

Referring now to FIG. 5, a block diagram of an example of a computer system 500 that can perform the methods described in the present disclosure is shown. The computer system 500 generally includes an input 502, at least one hardware processor 504, a memory 506, and an output 508. Thus, the computer system 500 is generally implemented with a hardware processor 504 and a memory 506.

In some embodiments, the computer system 500 can be a workstation, a notebook computer, a tablet device, a mobile device, a multimedia device, a network server, a mainframe, one or more controllers, one or more microcontrollers, or any other general-purpose or application-specific computing device.

The computer system 500 may operate autonomously or semi-autonomously, or may read executable software instructions from the memory 506 or a computer-readable medium (e.g., a hard drive, a CD-ROM, flash memory), or may receive instructions via the input 502 from a user, or any another source logically connected to a computer or device, such as another networked computer or server. Thus, in some embodiments, the computer system 500 can also include any suitable device for reading computer-readable storage media.

In general, the computer system 500 is programmed or otherwise configured to implement the methods and algorithms described in the present disclosure. For instance, the computer system 500 can be programmed to implement a self-navigated approach for correcting modulations in $k_z$-segmented 3D magnetic resonance data acquisitions.

The input 502 may take any suitable shape or form, as desired, for operation of the computer system 500, including the ability for selecting, entering, or otherwise specifying parameters consistent with performing tasks, processing data, or operating the computer system 500. In some aspects, the input 502 may be configured to receive data, such as data acquired with an MRI system. Such data may be processed as described above to correct for the effects of physiological changes occurring during the application of diffusion encoding gradients. In addition, the input 502 may also be configured to receive any other data or information considered useful for implementing the methods described above.

Among the processing tasks for operating the computer system 500, the one or more hardware processors 504 may also be configured to carry out any number of post-processing steps on data received by way of the input 502.

The memory 506 may contain software 510 and data 512, such as data acquired with an MRI system, and may be configured for storage and retrieval of processed information, instructions, and data to be processed by the one or more hardware processors 504. In some aspects, the software 510 may contain instructions directed to estimating relative phase values, computing and updating $k_z$-dependent phase values, and correcting magnetic resonance data based on those updated phase values.

In addition, the output 508 may take any shape or form, as desired, and may be configured for displaying images, in addition to other desired information.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

The present disclosure has described one or more preferred embodiments, and it should be appreciated that many equivalents, alternatives, variations, and modifications, aside from those expressly stated, are possible and within the scope of the invention.

The invention claimed is:

1. A method for reconstructing an image of a subject from k-space data acquired with a magnetic resonance imaging (MRI) system, the steps of the method comprising:

(a) accessing k-space data acquired from a subject using an MRI system, wherein the k-space data are segmented k-space data acquired comprising a plurality of k-space segments;

(b) estimating a reference phase map for each k-space segment from non-diffusion-weighted data in the k-space data for each $k_z$-plane;

(c) calculating k-space segment-dependent phase values from the k-space data;

(d) calculating phase difference values for each k-space segment using the reference phase map for that k-space segment and corresponding k-space segment-dependent phase values;

(e) generating phase corrected k-space data by applying the phase difference values to the k-space data in order to reduce phase corruptions caused by physiological changes in the subject that occurred when the k-space data were acquired; and (f) reconstructing an image from the phase corrected k-space data.

2. The method as recited in claim 1, wherein the reference phase values are channel-independent reference phase values.

3. The method as recited in claim 1, wherein the plurality of k-space segments comprise a plurality of $k_z$-planes and the k-space segment-dependent phase values are $k_z$-dependent phase values.

4. The method as recited in claim 1, wherein the plurality of k-space segments comprise a plurality of readout segments each comprising a k-space blade.

5. The method as recited in claim 1, wherein the acquired k-space data are three-dimensional k-space data acquired using a diffusion weighted acquisition and comprising data acquired in a plurality of $k_z$-planes.

6. The method as recited in claim 5, wherein the reference phase maps are estimated after Fourier transforming non-diffusion-weighted k-space data for a given $k_z$-plane along $k_x$ and $k_y$ directions.

7. The method as recited in claim 5, wherein the reference phase maps are estimated after Fourier transforming k-space data with lower diffusion weighting that other k-space data in the acquired k-space data for a given $k_z$-plane along $k_x$ and $k_y$ directions.

8. The method as recited in claim 1, wherein the acquired k-space data are three-dimensional k-space data acquired using a spin echo (SE)-echo planar imaging (EPI) acquisition and comprising data acquired in a plurality of $k_z$-planes.

9. The method as recited in claim 8, wherein the reference phase maps are estimated after Fourier transforming k-space data acquired with a SE-EPI for a given $k_z$-plane along $k_x$ and $k_y$ directions.

10. The method as recited in claim 9, wherein the reference phase maps are estimated and updated for a subsequent acquisition with similar contrast as the reference maps.

11. The method as recited in claim 1, wherein the k-space segment-dependent phase values are channel-independent k-space segment-dependent phase values.

12. The method as recited in claim 11, wherein the acquired k-space data are three-dimensional k-space data and the plurality of k-space segment comprise a plurality a $k_z$-planes, and wherein the k-space segment-dependent phase values are $k_z$-dependent phase values estimated after Fourier transforming the k-space data for a given $k_z$-plane along $k_x$ and $k_y$ directions.

13. The method as recited in claim 12, wherein the acquired k-space data are diffusion weighted k-space data and different $k_z$-dependent phase values are estimated for each of a plurality of different diffusion weighting b-values.

14. The method as recited in claim 1, wherein generating the phase corrected k-space data comprises applying the phase difference values to impose a consistent phase across all channels while maintaining channel specific phase variations.

15. The method as recited in claim 1, wherein the phase difference values are filtered before applying the phase difference values to generate the phase corrected k-space data.

16. The method as recited in claim 15, wherein the phase difference values are filtered using a Gaussian filter.

17. The method as recited in claim 15, wherein the phase difference values are filtered using a Hamming window filter.

18. The method as recited in claim 1, wherein the k-space data are acquired using a segmented 3D echo planar imaging (EPI) acquisition.

19. The method as recited in claim 18, wherein the segmented 3D EPI acquisition implement at least one multiband radio frequency (RF) pulse.

20. The method as recited in claim 18, wherein the segmented 3D EPI acquisition implements at least one frequency swept radio frequency (RF) pulse.

21. The method as recited in claim 1, wherein the k-space data are acquired using a non-Cartesian acquisition.

22. The method as recited in claim 1, wherein the k-space data are acquired using a readout segmented 2D echo planar imaging (EPI) acquisition.

23. The method as recited in claim 1, wherein the k-space data are acquired using a readout segmented 3D echo planar imaging (EPI) acquisition.

24. The method as recited in claim 1, wherein the k-space data are acquired using a 3D echo volume imaging (EVI) acquisition.

25. The method as recited in claim 1, wherein the k-space data are acquired using a 3D gradient and spin echo (GRASE) acquisition.

26. The method as recited in claim 1, wherein the k-space data are acquired using a gated acquisition in which segmented data are acquired in similar motion positions based on a triggering scheme.

* * * * *